US012738344B2

(12) United States Patent
Ashutosh et al.

(10) Patent No.: US 12,738,344 B2
(45) Date of Patent: Sep. 15, 2026

(54) METHOD FOR FINDING VARIANTS FROM TARGETED SEQUENCING PANELS

(71) Applicant: Agilent Technologies, Inc., Santa Clara, CA (US)

(72) Inventors: Ashutosh, San Jose, CA (US); Devendra Joshi, Santa Clara, CA (US); Christian A. Le Cocq, Menlo Park, CA (US)

(73) Assignee: AGILENT TECHNOLOGIES, INC., Santa Clara, CA (US)

( * ) Notice: Subject to any disclaimer, the term of this patent is extended or adjusted under 35 U.S.C. 154(b) by 1696 days.

(21) Appl. No.: 16/591,438

(22) Filed: Oct. 2, 2019

(65) Prior Publication Data

US 2020/0105371 A1 Apr. 2, 2020

Related U.S. Application Data

(63) Continuation of application No. 14/288,299, filed on May 27, 2014, now abandoned.

(60) Provisional application No. 61/859,625, filed on Jul. 29, 2013.

(51) Int. Cl.

| | |
|---|---|
| ***G16B 30/20*** | (2019.01) |
| ***C12Q 1/6869*** | (2018.01) |
| ***C12Q 1/6886*** | (2018.01) |
| ***G16B 30/00*** | (2019.01) |
| ***G16B 30/10*** | (2019.01) |

(52) U.S. Cl.

CPC ........... *G16B 30/20* (2019.02); *C12Q 1/6869* (2013.01); *C12Q 1/6886* (2013.01); *G16B 30/00* (2019.02); *G16B 30/10* (2019.02); *C12Q 2600/156* (2013.01)

(58) Field of Classification Search

None

See application file for complete search history.

(56) References Cited

U.S. PATENT DOCUMENTS

| | | | |
|---|---|---|---|
| 8,209,130 | B1 | 6/2012 | Kennedy et al. |
| 2005/0272086 | A1 | 12/2005 | Patil et al. |
| 2009/0111115 | A1 | 4/2009 | Drmanac et al. |
| 2010/0105052 | A1 | 4/2010 | Drmanac et al. |
| 2013/0110407 | A1 | 5/2013 | Baccash et al. |
| 2013/0184161 | A1 | 7/2013 | Kingsmore et al. |

FOREIGN PATENT DOCUMENTS

| | | | |
|---|---|---|---|
| CN | 1381591 | A | 11/2002 |
| CN | 1711358 | A | 12/2005 |
| CN | 101313078 | A | 11/2008 |
| CN | 101680027 | A | 3/2010 |
| JP | 2006515987 | A | 6/2006 |
| JP | 2010521156 | A | 6/2010 |
| JP | 2011520420 | A | 7/2011 |
| WO | 2004044700 | A2 | 5/2004 |
| WO | 2004050839 | A2 | 6/2004 |
| WO | 2007037678 | A2 | 4/2007 |
| WO | 2008115427 | A2 | 9/2008 |
| WO | 2009076238 | A2 | 6/2009 |
| WO | 2010059235 | A3 | 8/2010 |

OTHER PUBLICATIONS

Gao, et al., "False-Positive And False-Negative Problems In Mycobacterium Tuberculosis-Dna-Pcr Detection System", Journal of Gansu Sciences; vol. 12, No. 3, Sep. 2000, 64-66.

Lei, et al., "Clinical Significance of CR Technology in TB Diagnosis," Jiangxi J. Med Lab Sci; vol. 16, No. 2, Jun. 1998, 90-92.

Batzoglou, et al., "ARACHNE: A Whole-Genome Shotgum Assembler", Genome.cship.org; Genome Res. vol. 12, 2002, 177-189.

Boisvert, et al., "Ray: Simultaneous Assembly of Reads from a Mix of High-Throughput Sequencing Technologies", Journal of Computational Biology; vol. 17, No. 11, 2010, 1519-1533.

Casals, et al., "Next-generation sequencing approaches for genetic mapping of complex diseases", Journal of NeuroImmunology, vol. 248, No. 1, 2012, 10-22.

Dahl, et al., "Multigene amplification and massively parallel sequencing for cancer mutation discovery", PNAS, vol. 104, No. 22, May 29, 2007, 9387-9392.

Dohm, et al., "SHARCGS, a Fast and Highly Accurate Short-read Assembly Algorithm for De Novo Genomic Sequencing", Genome Res. 2007 vol. 17, Oct. 1, 2007, 1697-1706.

Vandin, et al., "Algorithms for Detecting significantly Mutated Pathways in Cancer", Journal of Computational Biology; vol. 18, N0. 3, Nov. 3, 2011, 507-522.

Grassi, et al., "Ultradeep Sequencing of a Human Ultraconserved Region Reveals Somatic and Constitutional Genomic Instability", Plos Biology, vol. 8, No. 1, Jan. 5, 2010, 1-11.

Zagordi, et al., "Error Correction of Next-generation Sequencing Data and Reliable Estimation of HIV Quasispecies", Nucleic Acids Research, vol. 38, No. 21, Jul. 29, 2010, 7400-7409.

Li, et al., "A New Approach for Detecting Low-level Mutations in Next-generation Sequence Data", Genome Biology, Biomed Central ltd., London, GB, vol. 13, No. 5, May 23, 2012, 15 pages.

(Continued)

*Primary Examiner* — Joseph Woitach

(57) ABSTRACT

Provided herein is a method for identifying a sequence variant in an enriched sample. In certain embodiments, this method may comprise: (a) obtaining: (i) a plurality of sequence reads from a sample that has been enriched for a genomic region and (ii) a reference sequence for the genomic region; (b) assembling the sequence reads to obtain a plurality of discrete sequence assemblies that correspond to potential variants; (c) determining which of the potential variants are true and which are artifacts by examining the sequence reads that make up each of the discrete sequence assemblies; (d) optionally determining whether each of the true potential variants contains a mutation that is known to be associated with the reference sequence; and (e) outputting a report indicating whether the sample comprises a sequence variant.

12 Claims, 2 Drawing Sheets

(56) References Cited

OTHER PUBLICATIONS

Lyon, et al., "Identifying Disease Mutations in Genomic Medicine Settings: Current challenges and How to Accelerate Progress", Lyon and Wang Genome Medicine vol. 4 No. 58, 2012, 1-16.
Mundry, et al., "Evaluating Characteristics of De Novo Assembly Software on 454 Transcriptome Data: A Simulation Approach", Plos One, vol. 7, No. 2, Feb. 27, 2012, 1-10.
Myers, et al., "A Whole-Genome Assembly of *Drosophila*", Science vol. 287, 2000, 2196-2204.
Peng, et al., "Multiple Sequence Assembly from Reads Alignable to a Common Reference Genome", IEEE/ACM Transactions on Computational Biology and Bioinformatics, IEEE Service Center, New York, NY, US, vol. 8, No. 5, Sep. 1, 2011, 1283-1295.
Raymond, et al., "Lessons Learnt from Large-scale Exon Resequencing of the X Chromosome", Human Molecular Genetics vol. 18, Review Issue 1, 2009, R60-R64.
SIPO, "Office Action mailed on Dec. 5, 2017", Application No. 201410355823.6, 7 pages.
Taub, et al., "Overcoming bias and systematic errors in next generation sequencing data", Genome Medicine, vol. 2, No. 12, Jan. 1, 2010, 1-5.
Teo, et al., "Statistical Challenges Associated with Detecting Copy Number Variations with Next-Generation Sequencing", Bioinformatics Advance Access vol. 28, Aug. 31, 2012, 2711-2718.
Van, et al., J Mol Diagn., Jan. 2010, 27-34.
Van Eijk, et al., "Sensitive and Specific KRAS Somatic Mutation Analysis on Whole-Genome Amplified DNA from Archival Tissues", Journal of Molecular Diagnostics, vol. 12, No. 1, Jan. 2010, 27-34.

METHOD FOR FINDING VARIANTS FROM TARGETED SEQUENCING PANELS

CROSS-REFERENCING

This application claims the benefit of U.S. provisional patent application Ser. No. 61/859,625, filed on Jul. 29, 2013, which application is incorporated by reference in its entirety.

BACKGROUND

A comprehensive detailing of mutations is indispensable for understanding, diagnosis and treatment of many diseases including cancers. A number of methods have been proposed for finding mutations from sequencing data, which usually consist of statistically evaluating the presence of variant bases compared to a reference. However, accurate determination of mutations remains a challenge in situations where a mutation is found only in a small fraction of reads. The delineation of such mutations is important especially in cancer. Such mutations are important not only for samples with low tumor content but are also important for capturing minor tumor sub clones to understand tumor heterogeneity and therefore the underlying causes of recurrence and therapeutic resistance.

Enrichment techniques are appealing for studying such samples due to the high uniformity and read depths possible. However, though the experimental techniques capture the information accurately, the existing analysis methods are not suited for detection of low frequency variants.

There are a number of other tools, both open source and commercial, that can call sequence variants. Attempt to use such tools for target enrichment data often tends to become cumbersome and does not use all characteristics of data resulting in erroneous calls or false positives and also missed calls. Furthermore, as noted in the literature, each method not only has its own shortcomings, but the calls are also discordant between different methods. Some methods only attempt to detect low frequency mutations when a matched normal sample is supplied and others call only SNPs and do not call insertions, deletions or multiple nucleotide polymorphisms (MNPs).

The problems are aggravated in case of low frequency variants in targeted sequencing at high read depths. Most of the methods work by looking at individual variant sites and assessing statistical significance of mutant at that position. For example, if an individual locus has 1000 read depth then on average one expects heterozygote calls to be covered by 500 reads to support a mutant allele. However, there would be places where a heterozygote genuinely exists but gets sampled a very few times. In case of mosaic samples, the mutations that are characteristics of minor components would have much lower frequency. Statistically, while sampling such a large sample space, rare events would occur and it becomes difficult to distinguish low frequency calls from sequencing errors. The problem gets further compounded by presence of other artifacts of amplification and capture. In presence of complex events and indels (insertions-deletions) in a genomic region, the reference sequence does not accurately represent the variant distribution and this leads to further artifacts. Many of the existing solutions try to address these issues by using multiple separate methods but from current literature, there is no solution that can reliably call these variants.

SUMMARY

Provided herein is a method for identifying a sequence variant in an enriched sample. In certain embodiments, this method may comprise: (a) obtaining: (i) a plurality of sequence reads from a sample that has been enriched for a genomic region and (ii) a reference sequence for the genomic region; (b) assembling the sequence reads to obtain a plurality of discrete sequence assemblies that correspond to potential variants; (c) determining which of the potential variants are true and which are artifacts by examining the sequence reads that make up each of the discrete sequence assemblies; (d) optionally determining whether each of the true potential variants contains a mutation that is known to be associated with the reference sequence; and (e) outputting a report indicating whether the sample comprises a sequence variant.

Also provided is a computer system comprising a memory comprising: a) a database of sequences; and b) an executable program for performing the present method.

Also provided is a computer-readable storage medium comprising instructions for performing the present method.

Also provided is a method of identifying a variant sequence. In certain embodiments, this method may comprise: a) inputting sequence information into a computer system comprising a program comprising instructions for performing the present method; b) executing the program; and c) receiving an output from the computer system.

These and other features of the present teachings are set forth herein.

BRIEF DESCRIPTION OF THE FIGURES

The skilled artisan will understand that the drawings, described below, are for illustration purposes only. The drawings are not intended to limit the scope of the present teachings in any way.

DEFINITIONS

Figure 1:
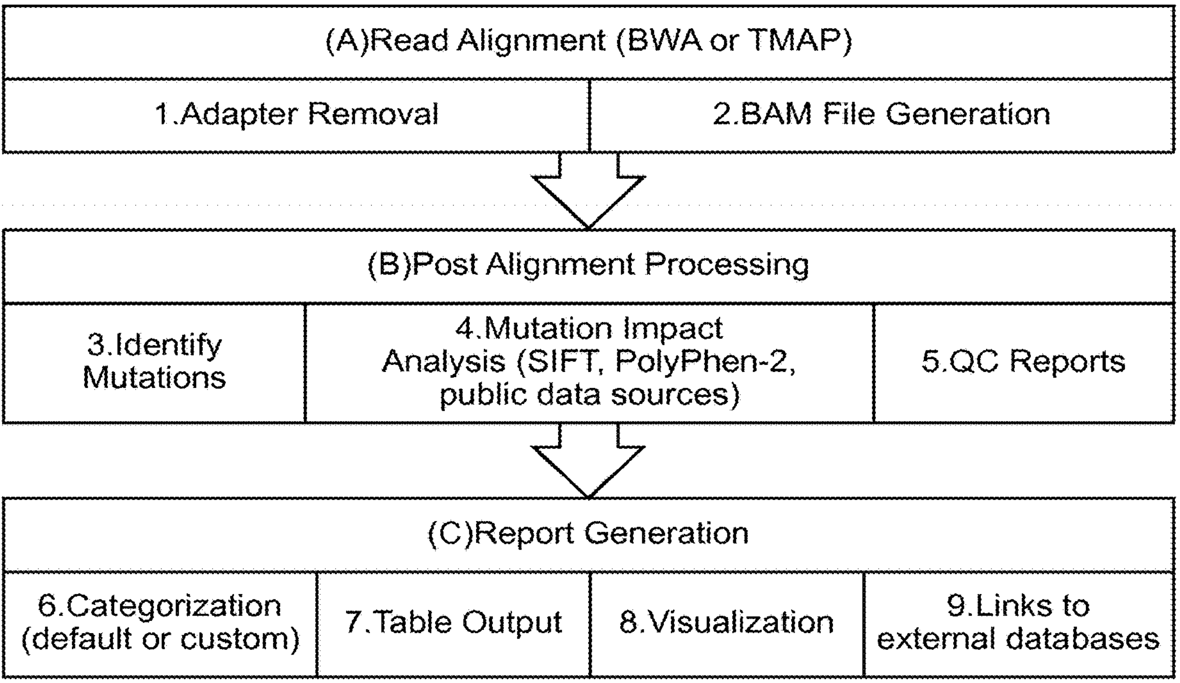
FIG. 1 is a flow chart illustrating one embodiment of the present method.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

The term "amplifying" as used herein refers to generating one or more copies of a target nucleic acid, using the target nucleic acid as a template.

As used herein, the term "single nucleotide polymorphism," or "SNP" for short, refers to a single nucleotide position in a genomic sequence for which two or more alternative alleles are present at appreciable frequency (e.g., at least 1%) in a population.

The term "enriching," with respect to a genome, refers to the separation of one or more regions of a genome from the remainder of the genome to produce a product that is isolated from the remainder of the genome. Enriching may be done using a variety of methods including those described in, e.g., Hedges et al (*Comparison of three targeted enrichment strategies on the SOLiD sequencing platform.* PLoS One 2011 6: e18595) and Shearer et al (*Solution-based targeted genomic enrichment for precious DNA samples BMC Biotechnol.* 2012 12: 20).

The term "enriched sample" refers to a sample that contains fragments of genomic DNA that have been isolated from the remainder of the genome, Enriched fragments can be of any length depending on the fragmentation method used. In certain embodiments, the fragments may be in the range of 100 bp to 1 kb in length, e.g., 200 bp to 500 bp in length, although fragments outside of this range may be used, Depending on how the fragmentation and/or enriching is done, for any one enriched region, the ends of the fragment molecules may be the same or different.

The term "genomic region," as used herein, refers to a region of a genome, an animal or plant genome such as the genome of a human, monkey, rat, fish or insect or plant.

A "plurality" contains at least 2 members. In certain cases, a plurality may have at least 10, at least 100, at least 1000, at least 10,000, at least 100,000, at least $10^6$, at least $10^7$, at least $10^8$ or at least $10^9$ or more members.

The term "sequencing," as used herein, refers to a method by which the identity of at least 10 consecutive nucleotides (e.g., the identity of at least 20, at least 50, at least 100 or at least 200 or more consecutive nucleotides) of a polynucleotide are obtained.

The term "next-generation sequencing" refers to the so-called parallelized sequencing-by-synthesis or sequencing-by-ligation platforms currently employed by Illumina, Life Technologies, and Roche, etc. Next-generation sequencing methods may also include nanopore sequencing methods or electronic-detection based methods such as Ion Torrent technology commercialized by Life Technologies.

The term "sequence reads" refers to the output of a sequencing run. Sequence reads are represented by a string of nucleotides. Sequence reads may be accompanied by metrics about the quality of the sequence. For example, each nucleotide in a sequence read may be associated with the confidence of the base call, i.e., a determination of whether a nucleotide is a G, A, T or C, for that nucleotide.

The term "sequence variant" refers to a nucleic acid sequence that is different from a reference sequence at at least one position. Examples of sequence variants include sequences containing SNPs and somatic mutations.

The terms "low frequency sequence variant," "minority species" and "minority variant" refer to a variant sequence that is only present in a sample at a frequency of less than 10% (e.g., less than 5% or less than 1%), relative to the non-variant version of the sequence. In many cases, a low frequency sequence may be represented by a nucleotide substitution or indel in a gene, and the non-variant version of the sequence will be represented by a wild type allele of the same gene. Low frequency sequence variants can be generated by somatic mutations, for example.

The term "reference sequence" refers to a known sequence, e.g., a sequence from a public or in-house database, to which a candidate sequence can be compared.

As used herein, the term "assembling" refers to a multi-step process that involves: aligning sequences that represent fragments of a longer nucleic acid. In certain cases, assembling may involve merging the sequences in order to construct the sequence of a segment.

As used herein, the term "anchor" refers to a sequence that is present in longer sequences that can be used to align those sequences. In certain cases, an anchor may be sufficient to correctly align the longer sequences.

As used herein, the term "sequence contig" refers to a contiguous sequence of nucleotides that is produced by assembling overlapping sequences.

A used herein, the term "associated with cancer" refers to a genomic region, e.g., a gene, that contains mutations correlated with a cancerous phenotype. In some cases, the mutations are believed to have a causative role in cancer.

DETAILED DESCRIPTION

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Where a range of values is provided, it is understood that each intervening value, to the tenth of the unit of the lower limit unless the context clearly dictates otherwise, between the upper and lower limit of that range and any other stated or intervening value in that stated range is encompassed within the present disclosure.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

It must be noted that as used herein and in the appended claims, the singular forms "a," "an," and "the" include plural referents unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

One with skill in the art will appreciate that the present invention is not limited in its application to the details of construction, the arrangements of components, category selections, weightings, pre-determined signal limits, or the steps set forth in the description or drawings herein. The invention is capable of other embodiments and of being practiced or being carried out in many different ways.

As noted above, the present method may be performed on sequence reads that have been obtained from an sample that has been enriched for a particular genomic region, i.e., a sample that contains fragments of genomic DNA that correspond to a particular genomic region, where the fragments have been enriched from fragmented total genomic DNA. In some cases, the enriched genomic region may contain a gene that has a mutation that is associated with one or more cancers, e.g., breast cancer, melanoma, renal cancer, endometrial cancer, ovarian cancer, pancreatic cancer, leukemia, colorectal cancer, prostate cancer, mesothelioma, glioma, medullobastoma, polycythemia, lymphoma, sarcoma or multiple myeloma, etc. (see, e.g., Chial *Proto-oncogenes to oncogenes to cancer.* Nature Education 2008 1:1). Genes of interest include, but are not limited to, PIK3CA, NRAS, KRAS, JAK2, HRAS, FGFR3, FGFR1, EGFR, CDK4, BRAF, RET, PGDFRA, KIT and ERBB2. In particular cases the sample may contain fragments of genomic DNA that correspond to multiple different genomic regions (e.g., several different regions, e.g., at least 2, at least 5, at least 10, at least 50, at least 100 or at least 1,000 or more different, non-overlapping, regions) that have been enriched, where each region may correspond to a gene, e.g., an oncogene.

The enriched genomic region may be enriched from an initial genomic sample using any convenient method, e.g., using hybridization to an oligonucleotide probe or using a ligation-based method. In some embodiments, the genomic region may be enriched by hybridization in solution to one or more biotinylated oligonucleotides (which, in certain cases, may be RNA oligonucleotides) that may be from 20 to 200 nt in length, e.g., 100 to 150 nt in length, to capture regions of interest. In these embodiments, after capture, duplexes containing fragments of genomic DNA that hybridize to the oligonucleotides may be isolated from other fragments using, e.g., streptavidin beads. In other embodiments, the region of interest may be enriched using the method described by Dahl et al (*Multiplex amplification enabled by selective circularization of large sets of genomic DNA fragments.* Nucleic Acids Res, 2005 33: e71). In this method, a genomic sample may be fragmented using one or more restriction enzymes and denatured. In this method, a probe library is hybridized to the targeted fragments. Each probe is an oligonucleotide designed to hybridize to both ends of a targeted DNA restriction fragment, thereby guiding the targeted fragments to form circular DNA molecules. The probe also contains a method-specific sequencing motif that is incorporated during circularization. In some cases, the probes are biotinylated and the targeted fragments can be retrieved using streptavidin beads. The circular molecules are then closed by ligation, a very precise reaction that ensures that only perfectly hybridized fragments are circularized. Next, the circular DNA targets are amplified. Other enrichment methods may be described in, e.g., Hedges et al (*Comparison of three targeted enrichment strategies on the SOLiD sequencing platform.* PLoS One 2011 6: e18595) and Shearer et al (*Solution-based targeted genomic enrichment for precious DNA samples BMC Biotechnol.* 2012 12: 20).

The genomic DNA may be isolated from any organism. The organism may be a prokaryote or a eukaryote. In certain cases, the organism may be a plant, e.g., Arabidopsis or maize, or an animal, including reptiles, mammals, birds, fish, and amphibians. In some cases, the initial genomic sample may be isolated from a human or rodent, such as a mouse or a rat. In exemplary embodiments, the initial genomic sample may contain genomic DNA from a mammalian cell, such as, a human, mouse, rat, or monkey cell. Methods of preparing genomic DNA for analysis is routine and known in the art, such as those described by Ausubel, F. M. et al., (*Short protocols in molecular biology,* 3rd ed., 1995, John Wiley & Sons, Inc., New York) and Sambrook, J. et al. (*Molecular cloning: A laboratory manual,* $2^{nd}$ ed., 1989, Cold Spring Harbor Laboratory Press, Cold Spring Harbor, N.Y.). The initial genomic sample may contain genomic DNA or an amplified version thereof (e.g., genomic DNA amplified by a whole genome amplification method using the methods of Lage et al (Genome Res. 2003 13: 294-307), Zong et al (Science. 2012 338: 1622-1626), or published patent application US20040241658, for example). Fragments may be made by fragmenting a genome using physical methods (e.g., sonication, nebulization, or shearing), chemically, enzymatically (e.g., using a rare-cutting restriction enzyme) or using a transposable element (see, e.g., Caruccio Methods Mol. Biol. 2011 733: 241-55; Kaper et al, Proc. Natl. Acad. Sci. 2013 110: 5552-7; Marine et al, Appl. Environ. Microbiol. 2011 77: 8071-9 and US2100120098).

The sample may be made from cultured cells or cells of a clinical sample, e.g., a tissue biopsy, scrape or lavage or cells of a forensic sample (i.e., cells of a sample collected at a crime scene). In particular embodiments, the nucleic acid sample may be obtained from a biological sample such as cells, tissues, bodily fluids, and stool. Bodily fluids of interest include but are not limited to, blood, serum, plasma, saliva, mucous, phlegm, cerebral spinal fluid, pleural fluid, tears, lactal duct fluid, lymph, sputum, cerebrospinal fluid, synovial fluid, urine, amniotic fluid, and semen. In particular embodiments, a sample may be obtained from a subject, e.g., a human, and it may be processed prior to use in the present method. For example, the nucleic acid may be extracted from the sample prior to use, methods for which are known. In particular embodiments, the genomic sample may be from a formalin fixed paraffin embedded (FFPE) sample.

Depending on which method is implemented, the initial sample (i.e., prior to enrichment) may contain fragments of genomic DNA that are already adaptor-ligated, In other embodiments, the fragments may be ligated to an adaptor after they have been enriched.

In some cases, samples may be pooled. In these embodiments, the fragments may have a molecular barcode to indicate their source, In some embodiments the DNA being analyzed may be derived from a single source (e.g., a single organism, virus, tissue, cell, subject, etc.), whereas in other embodiments, the nucleic acid sample may be a pool of nucleic acids extracted from a plurality of sources (e.g., a pool of nucleic acids from a plurality of organisms, tissues, cells, subjects, etc.), where by "plurality" is meant two or more. As such, in certain embodiments, the sample can contain nucleic acids from 2 or more sources, 3 or more sources, 5 or more sources, 10 or more sources, 50 or more sources, 100 or more sources, 500 or more sources, 1000 or more sources, 5000 or more sources, up to and including about 10,000 or more sources. Molecular barcodes may allow the sequences from different sources to be distinguished after they are analyzed.

After an enriched sample has been obtained, it is amplified and sequenced. In certain embodiments, the fragments are amplified using primers that are compatible with use in, e.g., Illumina's reversible terminator method, Roche's pyrosequencing method (454), Life Technologies' sequencing by ligation (the SOLiD platform) or Life Technologies' Ion Torrent platform. Examples of such methods are described in the following references: Margulies et al (Nature 2005 437: 376-80); Ronaghi et al (Analytical Biochemistry 1996 242: 84-9); Shendure et al (Science 2005 309: 1728-32); Imelfort et al (Brief Bioinform. 2009 10:60948); Fox et al (Methods Mol Biol. 2009; 553:79-108); Appleby et al (Methods Mol Biol. 2009; 513:19-39) and Morozova et al (Genomics. 2008 92:255-64), which are incorporated by reference for the general descriptions of the methods and the particular steps of the methods, including all starting products, reagents, and final products for each of the steps.

In one embodiment, the isolated product may be sequenced using nanopore sequencing (e.g. as described in Soni et al. 2007 Clin. Chem. 53: 1996-2001, or as described by Oxford Nanopore Technologies). Nanopore sequencing is a single-molecule sequencing technology whereby a single molecule of DNA is sequenced directly as it passes through a nanopore. A nanopore is a small hole, of the order of 1 nanometer in diameter. Immersion of a nanopore in a conducting fluid and application of a potential (voltage) across it results in a slight electrical current due to conduction of ions through the nanopore. The amount of current which flows is sensitive to the size and shape of the nanopore. As a DNA molecule passes through a nanopore, each nucleotide on the DNA molecule obstructs the nanopore to a different degree, changing the magnitude of the current through the nanopore in different degrees. Thus, this change in the current as the DNA molecule passes through the nanopore represents a reading of the DNA sequence. Nanopore sequencing technology is disclosed in U.S. Pat. Nos. 5,795,782, 6,015,714, 6,627,067, 7,238,485 and 7,258,838 and U.S. Pat Appln Nos. 2006003171 and 20090029477.

In some embodiments, the sequencing may produce, for each enriched region at least 100, at least 1,000, at least 10,000 up to 100,000 or more sequence reads. The length of the sequence reads may vary greatly depending on, for example, the platform used. In some embodiments, the length of sequence reads may be in the region of 30 to 800 bases and, in some cases, may include paired end reads.

The sequence reads can be assembled to obtain a plurality of discrete sequence assemblies that each corresponds to a potential variant using a variety of different methods. Sequence reads may be assembled using any suitable method, basic steps of which are described in a variety of publications such as Myers et al (Science 2000 287: 2196-204), Batzoglou et al (Genome Research 2002 12: 177-89), Dohm et al (Genome Research 2007 17: 1697-706) and Boisvert et al (Journal of Computational Biology 2010 17: 1.519-33), which are all incorporated by reference for disclosure of those methods. In some embodiments, for each enriched region, the sequence reads can be assembled to produce a single pile-up that is examined to identify sequence reads that have a nucleotide variation (e.g., a substitution, insertion or deletion) at a particular position. Sequence reads that have a nucleotide variation at a particular nucleotide position can then be re-assembled as a discrete sequence assembly. In other embodiments, the sequences may be assembled at high stringency, i.e., in a way in which sequence reads that have the same variation will cause the sequences to group with one another. In yet other embodiments, sequence reads can be assembled by aligning each read to a reference sequence, such as a reference genome. In certain cases, at least one assembled sequence obtained from the sequence reads aligns to the reference sequence.

In some cases and as will be described in greater detail below, graph theory is used to assemble the reads. In particular cases, assembling the sequence reads may comprise making a directed graph, such as a de Bruijn graph. For example, constructing a de Bruijn graph of sequence reads may involve: collecting overlapping k-mers from the sequencing reads, including subsequences of length k within the reads, in a target region; splitting each k-mer into two overlapping (k−1)-mers; and assigning a vertex or node of the graph to each (k−1)-mer and an edge connecting the two nodes in the graph to the k-mer. Thus each sequence read is represented in the graph as a path through the k-mers, and a potential sequence contig may be represented in the graph by joining multiple paths through the k-mers. The use of de-Bruijn graphs to assemble reads is described in U.S. Pat. No. 8,209,130; U.S. Pub. 2011/0004413, U.S. Pub. 2011/0015863, and U.S. Pub. 2010/0063742, which are incorporated by reference herein.

In certain cases the directed graph may be a directed weighted graph. In certain aspects, the directed weighted graph is constructed using k-mers of the same length. In certain embodiments, the choice of which edge to select to construct a potential sequence at a node is made without using a cutoff value that is a function of the read coverage at the particular node or edges connected to the node.

A potential sequence is represented in the directed weighted graph by an Euler path. Thus, assembling the sequence reads may further involve finding an Euler path through the directed weighted graph constructed from the sequence reads. Finding an Euler path through the directed weighted graph may comprise finding a minimal de-Bruijn sequence (i.e., cyclic sequence of a given alphabet A with size k for which every possible subsequence of length n in A appears as a sequence of consecutive characters exactly once) in a language with forbidden strings. See, e.g., Moreno et al., Graph-Theoretic Concepts in Computer Science 2004 3353:168). In such cases, a minimum de-Bruijn may be defined by a spanning subgraph, or tree of the directed weighted graph, using the BEST (de Bruijn, Ehrenfest, Smith and Tutte) theorem (which provides a product formula for the number of Eulerian circuits in directed (oriented) graphs, and relates the number of Eulerian circuits to the number of rooted spanning trees at a given vertex). Determining spanning trees of a directed graph may be achieved by any convenient method (see, e.g., Tarjan et al. Proc FOCS 1984 12-20). Representation of the weighted directed graph as a de-Bruijn sequence with forbidden words leads to an estimate of the maximum number of words possible in the graph and reflects the information entropy of the directed graph. This entropic bound is also a limit on the eigenvalue of the transition matrix of the directed graph. As the bound for information entropy is determined by the directed graph constructed from the sequence reads, any potential variant sequence that cannot be derived, given the set of sequencing reads, from a reference or a another potential variant without exceeding the information entropy bound (i.e. if the eigenvalue for the transition matrix between the potential variant and another variant or reference exceeds the bound established above) will be discarded.

In certain cases, the sequence reads may be anchored on a reference sequence, which will be discussed in greater detail below. In some embodiments the sequence assembly method involves, in each of the sequence reads, demarcating the regions where sequencing is deemed reliable, and each of the assemblies may be anchored using the reference sequence as well as sequences that are local to the reference sequence.

In this method, the sequence assembly step results in a plurality of discrete assemblies, where each assembly corresponds to a potential variant. Each potential variant is defined by a sequence variation that is found in the sequence reads. As such, all of the candidate sequences in a discrete assembly have the same variation. Any one enriched region may be represented by at least 2, at least 5, at least 10, at least 15, at least 20, at least 30, at least 50, at least 100 or more discrete assemblies. The number of sequence reads in each assembly may vary greatly. In several cases, the majority of sequence reads may assemble into one or two assemblies that represent the dominant variants in the sample (depending on whether the original sample from which the genomic DNA was originally obtained is homozygous or heterozygous for a germline difference, e.g., a SNP, in the enriched region). The remaining assemblies may correspond to low frequency variant sequences (e.g., sequences obtained from somatically mutated cells), may be derived from PCR errors, and/or may contain mis-called bases. In certain cases, these assemblies may be represented by fewer sequence reads that contain the variation (e.g., 10 to 1,000 or more, depending on the total number of sequence reads that are obtained).

In the next step of the method, the discrete assemblies are screened to determine which of the potential variants are "true" (i.e., correctly provide the sequence for a molecule in the sample and are not the result of an error in the sequencing reaction or data processing, e.g., a base mis-call) and which candidate molecules are artifacts (i.e., are the result of an error in the sequencing reaction or data processing, e.g., a base mis-call, and not the actual sequence of a molecule in the sample). This step may be done by examining the sequence reads that make up each of the discrete sequence assemblies. In some embodiments, this step may be done by examining a variety of parameters, including read quality, the confidence of a base call, and confidence of an alignment (i.e., whether the sequence has mapped to the right location). Weakly defined candidate molecules (i.e., candidate molecules that are defined by poor sequence reads, candidate molecules in which the sequence variant is represented by a low confidence base call, etc.) can be dissolved, and the sequence can be merged with other alignments. In certain embodiments, the likelihood of each potential variant, given the set of sequencing reads, is assigned using a Hidden Markov model. In some embodiments, this step may comprise examining the quality of a sequence, the number of reads, the quality of base calls and their match to the reference sequence, to provide a score for each of the potential variants.

Once the true potential variants have been identified, the mutations defined by the potential variants can be optionally compared to the known mutations for a reference sequence, where the reference sequence is a sequence from a public or in-house database. In certain embodiments the comparing involves determining whether each of the true potential variants contains a mutation that is known to be associated with the reference sequence. For example, the identity of several thousand cancer-associated mutations in several hundred genes can be found at the Sanger Center's COSMIC database (see also Jung et al *Systematic investigation of cancer-associated somatic point mutations in SNP databases Nature Biotechnology* 2013 31: 787-789). For example, if the enriched sequence includes sequences from the KRAS gene, then the true variants can be analyzed to determine whether any of them have any of the following mutations: 35G>A, 35G>T, 38G>A, 34G>T, 35G>C, 34G>A, 34G>C, 37G>T, 183A>C, 37G>A, 182A>T, 183A>T, 436G>A, 37G>C, 182A>G, 34_35GG>TT, 38G>C, 181C>A, 38_39GC>AT, or 38G>T. These mutations are found at high rates in leukemias, colorectal cancer (Burmer et al. Proc. Natl. Acad. Sci. 1989 86: 2403-7), pancreatic cancer (Almoguera et al. Cell 1988 53: 549-54) and lung cancer (Tam et al. Clin. Cancer Res. 2006 12: 1647-53). Likewise, if the enriched sequence includes sequences from the NRAS gene, the true candidate molecules can be analyzed to determine whether any of them have any of the following mutations in NRAS: 182A>G, 181C>A, 35G>A, 182A>T, 38G>A, 34G>A, 37G>C, or 1849G>T.

In certain embodiments, the method may involve enriching for one or more pairs of genomic regions, where each pair of genomic regions is composed of a genomic region of interest (e.g., a cancer-associated gene) and a region that is adjacent to (and, in some cases, overlapping with) the genomic region of interest, In these embodiments, the pair may be enriched separately and combined prior to amplification. The sequence reads for each pair can be analyzed together. The reads for the second genomic region allows one to average statistics over a longer length, leading to better results. In some cases, the sequence reads for the adjacent region can be used to, for example, adjust the results to accommodate any sampling bias.

The method may comprise outputting a report indicating whether the sample comprises a particular sequence variant. The report may contain an indication of whether the sample contains a mutation, as well as available public information about the reference sequence and the mutation. In some cases, the report may indicate the confidence that the mutation is in the sample.

The above-described method may be employed to characterize, classify, differentiate, grade, stage, diagnose, or prognose a condition, or to predict a response to treatment. In particular cases, the method may be used to investigate a cancerous condition or another mammalian disease, including but not limited to, leukemia, breast carcinoma, prostate cancer, Alzheimer's disease, Parkinson's disease, epilepsy, amyotrophic lateral sclerosis, multiple sclerosis, stroke, autism, mental retardation, and developmental disorders. Many nucleotide polymorphisms are associated with and are thought to be a factor in producing these disorders. Knowing the type and the location of the nucleotide polymorphism may greatly aid the diagnosis, prognosis, and understanding of various mammalian diseases. In addition, the assay conditions described herein can be employed in other nucleic acid detection applications including, for example, for the detection of infectious diseases, viral load monitoring, viral genotyping, environmental testing, food testing, forensics, epidemiology, and other areas where specific nucleic acid sequence detection is of use.

In some embodiments, a biological sample, e.g., a biopsy, may be obtained from a patient, and the sample may be analyzed using the method. In particular embodiments, the method may be employed to identify and/or estimate the amount of mutant copies of a genomic locus that are in a biological sample that contains both wild type copies of a genomic locus and mutant copies of the genomic locus that have a point mutation relative to the wild type copies of the genomic locus. In this example, the sample may contain at least 100 times (e.g., at least 1,000 times, at least 5,000 times, at least 10,000 times, at least 50,000 times or at least 100,000 times) more wild type copies of the genomic locus than mutant copies of the genomic locus.

In these embodiments, the method may be employed to detect an oncogenic mutation (which may be a somatic mutation) in, e.g., PIK3CA, NRAS, KRAS, JAK2, HRAS, FGFR3, FGFR1, EGFR, CDK4, BRAF, RET, PGDFRA, KIT or ERBB2, which mutation may be associated with breast cancer, melanoma, renal cancer, endometrial cancer, ovarian cancer, pancreatic cancer, leukemia, colorectal cancer, prostate cancer, mesothelioma, glioma, medullobastoma, polycythemia, lymphoma, sarcoma or multiple myeloma (see, e.g., Chial Proto-oncogenes to oncogenes to cancer, Nature Education 2008 1:1).

Because the point mutation in a genomic locus may have a direct association with cancer, the subject method may be employed to diagnose patients with cancer or a pre-cancerous condition (e.g., adenoma etc.), alone, or in combination with other clinical techniques (e.g., a physical examination, such as, a colonoscopy or mammogram) or molecular techniques (e.g., immunohistochemical analysis). For example, results Obtained from the subject assay may be combined with other information, e.g., information regarding the methylation status of other loci, information regarding rearrangements or substitutions in the same locus or at a different locus, cytogenetic information, information regarding rearrangements, gene expression information or information about the length of telomeres, to provide an overall diagnosis of cancer or other diseases.

In one embodiment, a sample may be collected from a patient at a first location, e.g., in a clinical setting such as in a hospital or at a doctor's office, and the sample may be forwarded to a second location, e.g., a laboratory where it is processed and the above-described method is performed to generate a report. A "report" as described herein, is an electronic or tangible document which includes report elements that provide test results that may include a Ct value, or Cp value, or the like that indicates the presence of mutant copies of the genomic locus in the sample. Once generated, the report may be forwarded to another location (which may the same location as the first location), where it may be interpreted by a health professional (e.g., a clinician, a laboratory technician, or a physician such as an oncologist, surgeon, pathologist), as part of a clinical diagnosis.

Figure 2:
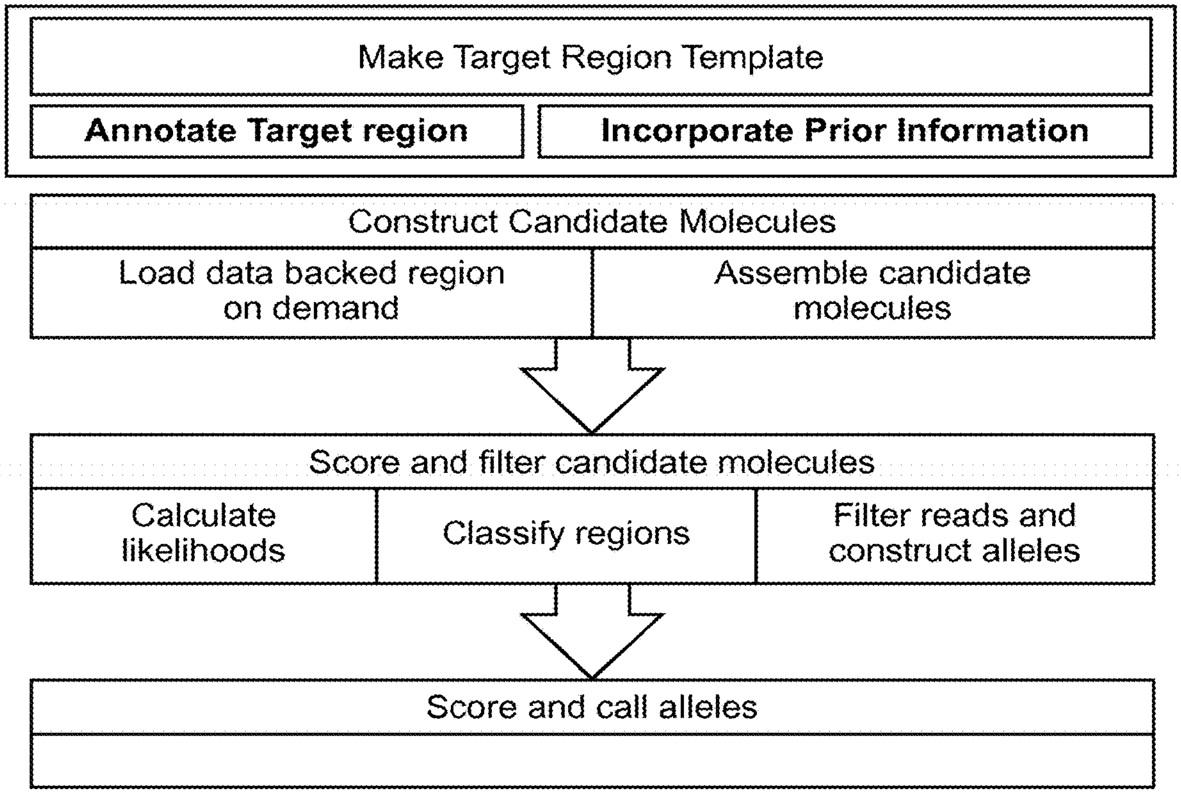
FIG. 2 is a flow chart illustrating another embodiment of the present method.

One implementation of the method is described in the flow charts of FIGS. 1 and 2. The first flow describes the overall setting of the method, e.g., the overall workflow. The second flow describes the flow of the method itself Each component of the method is then detailed. The method described below is an implementation of step B3 and is relevant to step B4 and step C parts 6 and 7 as well. In one implementation the method pertains to B3 i.e. identification of variants, both single nucleotide polymorphisms and insertion and deletions. The flow for the invention is described and detailed in FIG. 2.

In step 1, the design information is collected and used to annotate the regions of interest. The design information is utilized in the following way: the regions of interest are demarcated and the subregions where baits are placed are specified within the region of interest. The regions where sequencing could be reliable are obtained and marked. Optionally one could pad the regions to include a specified number of bases on both ends of the regions of interest to evaluate off target match of reads and also to point reference anchor points for subsequent steps. Typical reference sequence(s) are obtained as a template. If one wants to include any previously known information about variants in the given region, such variants are marked within the specified. region as well. Each non overlapping region is constructed and analyzed (in subsequent steps) in parallel by using the Java 7 Fork-Join framework for an efficient use of computational resources. At this step, the "region" is only a genomic template and data is loaded on demand as and when needed. In the second step, one tries to find all the relevant alternative stretches of molecular sequences that can be reliably constructed in such regions. First candidate reference sequences(s) are read from a supplied reference sequence. The method assumes that there is at least one molecular representation available that is exactly the same as reference. If there are more than one such representations available, all are constructed and evaluated below. Then, all alternative representations are constructed. This is done by locally re-assembling the reads in the target region. For this re-assembly, we use a number of results from symbolic sequences theory that result in optimization and fast determination of the candidate molecule sequences. First, a directed weighted graph is constructed out of overlapping k-mers. Any candidate molecule has to be represented in this graph as an Euler path (i.e. where each of edges is visited or in other words, edge traversal is complete) The "missed" or "non-sequenced" regions are assumed to be the same as reference and both mates of a paired end run are utilized where available. In cases where only one of the pair is mapped reliably, the method looks at all unmapped reads and tries to construct the candidate representation utilising k-mers so that local re-alignment is implicitly done.

To do this efficiently, theoretical results are used. Recognizing that the problem of finding candidate solutions is equivalent to finding the minimal de-Bruijn sequence in a language with forbidden strings, we note that there is a bound that relates number of "words" of a specific length to the estimation of information entropy. This entropic bound is also a bound on the largest eigenvalue of the transfer matrix specifying transitions between different k-mers (i.e. the largest eigenvalue is the natural log of the information). Therefore, while constructing a graph representing various candidates, a count of the number of allowed words of a given length can be considered. In some cases, a count of the number of forbidden words (the ones that do not occur) may be considered which, along with the total number of words possible gives us the desired information. The forbidden words can be easily found while constructing the graph itself. The bound on the largest eigenvalue can be used to speed up the calculation of likelihoods in the next step.

Applicant notes the publication does not properly depict the Bayes Theorem as filed in the publication. Applicant presents the properly depicted Bayes Theorem as shown below and depicted in the originally filed specification.

$$P(R_i|G_i) = \sum_{\forall(R_i \in G_i)} \left( \frac{s_i!}{\prod_{j=\lambda}^{k_i} d'_j!} \prod_{j=1}^{k_i} \left( \frac{f_{i_j}}{m_i} \right)^{o'_j} \prod_{l=1}^{s_i} P\left(b'_l | b_l\right) \right)$$

The second result that is used relies on the BEST theorem or the de Bruijn, Ehrenfest, Smith and Tutte Theorem. This theorem relates the possible Euler paths to the number of spanning trees in the graph. Since our aim is to construct Euler paths, the theorem transforms the problem into problem of finding spanning trees, which is a well known problem with fast solutions available. Vishkin's formulation can be used to find the spanning trees.

Since the graph could be unbalanced, the above results, though considerably speeding up the computation, may miss some paths, especially in situations where there are many multiply matched reads or structural and copy number variations are present. To guard against such corner cases, we count the paths where the incoming and outgoing weights differ from average significantly. If such paths are found then we do an exhaustive search for Euler paths on the subset of k-mers represented in such paths.

After the candidate molecule representations have been found, the likelihood is assigned to each using a markov model. In this we look at read (pairs) and evaluate which of the candidate molecules is most likely given the data. Reads that are used for this evaluation are first filtered by a specified filtering criteria on mapping quality. The transitions between candidates are represented as a transfer matrix and optimize the transitions based on the read data in the region. While doing this we use the eigenvalue bound above to quickly terminate any iteration that would result in a solution inconsistent with the bound. The emission and transition probabilities are determined by standard Viterbi iterations except for this speedup. A specified number of best scoring candidates can be examined.

After this step the various alleles present in the candidate solutions can be examined to make a variant call. The alleles that are found to be supported by bases too close to the ends of reads ("dose" defined by a parameter) are filtered out. Also if a variant candidate is at the end of an amplicon fragment and there is only one amplicon covering the locus, it is filtered out. In cases where more than one amplicons support that locus, such a candidate is kept only if it is supported by more than one amplicon.

Each variant is scored. In other words, given a set of reads {R} and a set of genotypes {G} we want to find P({G}|{R}). To do this, we uses Bayes Theorem i.e. obtain P({R}|{G}) and P({G}) and combine them to obtain the desired result:

$$P(R_i \mid G_i) = \sum_{\forall(R_i \in G_i)} \left( \frac{s_i!}{\prod_{j=1}^{k_i} o'_j!} \prod_{j=1}^{k_i} \left( \frac{f_{ij}}{m_i} \right)^{o'_j} \prod_{l=1}^{s_i} P(b'_l \mid b_l) \right)$$

i.e the probability of obtaining a set of reads given an underlying genotype is proportional to the probability of sampling the set of observations from the underlying genotype, scaled by the probability that our reads are correct. The term under the product P (b'|b) is the probability that a given alternative call at a given locus is correct. Since the quality of a base in a given read gives us the probability that the particular base in that read is correct and that we have filtered out poorly mapping reads, we assume that the quality of the allele is the minimum of median qualities of the bases and median mapping quality. Optionally we can use the base allele quality (BAQ) for this estimate. Then P(b'|b) is 1−q if b ϵ{G} and q otherwise.

P({G}) from the candidate molecule likelihood (which is the likelihood of seeing G1 . . . Gn) has already been obtained. To call a variant at a locus we want to look at the sites where there is more than one allele across the candidate regions and P(G(i)|{R}(i)) is significant. We already have the probability of various candidates being different from the reference and thus $$P(K>1|R1, \ldots, Rn)=1-P(K=1|R1, \ldots, Rn)$$

gives us the probability of a variant call.

This method may be used by clinical researchers looking for a fast, accurate and easy-to-use analysis tool for target enrichment panels. This software reduces the time to results from days to hours by providing an end-to-end data analysis solution: from alignment to categorization of mutations. This method is advantageous over previous algorithms because the rate of false negative in calling mutations is much lower without affecting the rate of false positives for a majority of the test samples, the method can detect variants with low allele frequency even in complex cases involving multiple alleles and at the same time does not increase the false positive rates significantly, and in detecting the low frequency mutations, the efficiency and speed is not significantly degraded.

The above-described method can be implemented on a computer. In certain embodiments, a general-purpose computer can be configured to a functional arrangement for the methods and programs disclosed herein. The hardware architecture of such a computer is well known by a person skilled in the art, and can comprise hardware components including one or more processors (CPU), a random-access memory (RAM), a read-only memory (ROM), an internal or external data storage medium (e.g., hard disk drive). A computer system can also comprise one or more graphic boards for processing and outputting graphical information to display means. The above components can be suitably interconnected via a bus inside the computer. The computer can further comprise suitable interfaces for communicating with general-purpose external components such as a monitor, keyboard, mouse, network, etc. In some embodiments, the computer can be capable of parallel processing or can be part of a network configured for parallel or distributive computing to increase the processing power for the present methods and programs. In some embodiments, the program code read out from the storage medium can be written into a memory provided in an expanded board inserted in the computer, or an expanded unit connected to the computer, and a CPU or the like provided in the expanded board or expanded unit can actually perform a part or all of the operations according to the instructions of the program code, so as to accomplish the functions described below. In other embodiments, the method can be performed using a cloud computing system. In these embodiments, the data files and the programming can be exported to a cloud computer, which runs the program, and returns an output to the user.

A system can in certain embodiments comprise a computer that includes: a) a central processing unit; b) a main non-volatile storage drive, which can include one or more hard drives, for storing software and data, where the storage drive is controlled by disk controller; c) a system memory, e.g., high speed random-access memory (RAM), for storing system control programs, data, and application programs, including programs and data loaded from non-volatile storage drive; system memory can also include read-only memory (ROM); d) a user interface, including one or more input or output devices, such as a mouse, a keypad, and a display; e) an optional network interface card for connecting to any wired or wireless communication network, e.g., a printer; and f) an internal bus for interconnecting the aforementioned elements of the system.

The memory of a computer system can be any device that can store information for retrieval by a processor, and can include magnetic or optical devices, or solid state memory devices (such as volatile or non-volatile RAM). A memory or memory unit can have more than one physical memory device of the same or different types (for example, a memory can have multiple memory devices such as multiple drives, cards, or multiple solid state memory devices or some combination of the same). With respect to computer readable media, "permanent memory" refers to memory that is permanent. Permanent memory is not erased by termination of the electrical supply to a computer or processor. Computer hard-drive ROM (i.e., ROM not used as virtual memory), CD-ROM, floppy disk and. DVD are all examples of permanent memory. Random Access Memory (RAM) is an example of non-permanent (i.e., volatile) memory. A file in permanent memory can be editable and re-writable.

Operation of the computer is controlled primarily by an operating system, which is executed by the central processing unit. The operating system can be stored in a system memory. In some embodiments, the operating system includes a file system. In addition to an operating system, one possible implementation of the system memory includes a variety of programming files and data files for implementing the method described below. In certain cases, the programming can contain a program, where the program can be composed of various modules, and a user interface module that permits a user to manually select or change the inputs to or the parameters used by the program. The data files can include various inputs for the program.

In certain embodiments, instructions in accordance with the method described herein can be coded onto a computer-readable medium in the form of "programming," where the term "computer readable medium" as used herein refers to any storage or transmission medium that participates in providing instructions and/or data to a computer for execution and/or processing, Examples of storage media include a floppy disk, hard disk, optical disk, magneto-optical disk, CD-ROM, CD-R, magnetic tape, non-volatile memory card, ROM, DVD-ROM, Blue-ray disk, solid state disk, and network attached storage (NAS), whether or not such devices are internal or external to the computer. A file containing information can be "stored" on computer readable medium, where "storing" means recording information such that it is accessible and retrievable at a later date by a computer.

The computer-implemented method described herein can be executed using programs that can be written in one or more of any number of computer programming languages. Such languages include, for example, Java (Sun Microsystems, Inc., Santa Clara, Calif.), Visual Basic (Microsoft Corp., Redmond, Wash.), and C++ (AT&T Corp., Bedminster, N.J.), as well as any many others.

In any embodiment, data can be forwarded to a "remote location," where "remote location," means a location other than the location at which the program is executed. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the interact or including email transmissions and information recorded on websites and the like.

Some embodiments include implementation on a single computer, or across a network of computers, or across networks of networks of computers, for example, across a network cloud, across a local area network, on hand-held computer devices, etc. Preferred embodiments include implementation on computer program(s) performing one or more of the steps described herein, Such computer programs execute one or more of the steps described herein. Preferred embodiments of the invention include various data structures, categories, and modifiers described herein, encoded on computer-readable medium(s) and transmissible over communications network(s).

Software, web, Internet, cloud, or other storage and computer network implementations of the present invention could be accomplished with standard programming techniques to accomplish the various database searching, modifying, correlating, comparing, deciding, signaling, scoring, surveilling, or ranking steps.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

What is claimed is:

1. A computer-implemented method performed by one or more computer processors to identify a low-frequency sequence variant corresponding to a somatic mutation associated with cancer in an enriched nucleic acid sample, the method comprising:

(a) obtaining (i) a plurality of sequence reads from a sample that has been enriched for a human genomic region associated with cancer, wherein the human genomic region comprises at least a portion of at least one of the following genes: PIK3CA, NRAS, KRAS, JAK2, HRAS, FGFR3, FGFR1, EGFR, CDK4, BRAT, RET, PGDFRA, KIT and ERBB2, and (ii) a reference sequence;

(b) assembling the sequence reads to obtain a plurality of discrete sequence assemblies by:

(i) constructing a directed weighted graph from overlapping k-mers of the plurality of sequence reads;

(ii) demarcating the region in each of the plurality of sequence reads where the sequence is deemed reliable;

(iii) identifying Eulerian paths in through the directed weighted graph by finding a minimal de Bruijin sequence with forbidden strings, wherein the minimal de-Bruijin sequence is determined using the BEST theorem by determining spanning trees of the directed weighted graph; and (iv) generating, from the identified Euler paths, the plurality of discrete sequence assemblies, wherein each assembly corresponds to a potential variant sequence supported by the sequence reads;

(c) determining which of the potential variants are true and which are artifacts by:

(i) evaluating the sequence reads that make up each of the discrete sequence assemblies by examining the sequence reads that make up each of the discrete sequence assemblies;

(ii) filtering the sequencing reads supporting each discrete assembly by a specified filtering criteria on mapping quality;

(iii) calculating likelihood scores for each potential variant using a hidden Markov model that evaluates read quality, confidence of base calls, and confidence of alignment of the filtered reads supporting the assembly; and, (iv) discarding as artifacts those potential variants that are weakly defined based on the likelihood;

(d) comparing the true variants known to be cancer-associated mutations to the reference sequence; and (e) outputting a report indicating whether said enriched nucleic acid comprises the low-frequency sequence variant.

2. The method of claim 1, wherein the somatic mutation is present at a frequency of less than 10% in a sample relative to the non-variant of the sequence.

3. The method of claim 1, wherein the enriched nucleic acid is enriched from total DNA obtained from a clinical sample.

4. The method of claim 3, wherein the clinical sample is a biopsy.

5. The method of claim 1, wherein the report provides an indication of whether the sample contains a mutation, as well as available public information about the reference sequence.

6. The method of claim 1, wherein said assembling uses graph theory.

7. The method of claim 1, wherein the reference sequence is annotated to identify mutations that are known in the art and where sequencing reads are likely to be.

8. The method of claim 1, wherein said assembling uses sequences that are from said reference sequence and sequences that are local to said reference sequence in order to anchor the assemblies.

9. The method of claim 1, wherein said method provides a probability for a variant call.

10. A computer system comprising a memory comprising:

(a) a database of sequence reads from a sample that has been enriched for a genomic region;

(b) a reference sequence for the genomic region; and (c) an executable program for performing the method of claim 1.

11. A computer readable storage medium comprising instructions for performing the method of claim 1.

12. A method of identifying a variant sequence, comprising:

(a) inputting sequence information into a computer system comprising a program comprising instructions for performing the method of claim 1;

(b) executing the program; and (c) receiving an output from the computer system.

* * * * *